US012779136B2

(12) United States Patent
Stefanov

(10) Patent No.: US 12,779,136 B2
(45) Date of Patent: Nov. 3, 2026

(54) MEDICAMENT DELIVERY DEVICE

(71) Applicant: SHL Medical AG, Zug (CH)

(72) Inventor: Slobodan Stefanov, Deerfield Beach, FL (US)

(73) Assignee: SHL Medical AG, Zug (CH)

(*) Notice: Subject to any disclaimer, the term of this patent is extended or adjusted under 35 U.S.C. 154(b) by 374 days.

(21) Appl. No.: 18/681,695

(22) PCT Filed: Aug. 4, 2022

(86) PCT No.: PCT/EP2022/072041

§ 371 (c)(1),
(2) Date: Feb. 6, 2024

(87) PCT Pub. No.: WO2023/016933

PCT Pub. Date: Feb. 16, 2023

(65) Prior Publication Data

US 2024/0366884 A1 Nov. 7, 2024

Related U.S. Application Data

(60) Provisional application No. 63/232,750, filed on Aug. 13, 2021.

(30) Foreign Application Priority Data

Aug. 31, 2021 (EP) .................................... 21194047

(51) Int. Cl.
*A61M 5/32* (2006.01)

(52) U.S. Cl.
CPC ................................ *A61M 5/3243* (2013.01)

(58) Field of Classification Search
CPC .................................................. A61M 5/3243
See application file for complete search history.

(56) References Cited

U.S. PATENT DOCUMENTS 4,717,383 A 1/1988 Phillips
7,789,856 B2 9/2010 Hillios
(Continued)

FOREIGN PATENT DOCUMENTS

EP 2588169 B1 4/2016
EP 2544739 B1 4/2017
(Continued)

OTHER PUBLICATIONS

International Search Report and Written Opinion for corresponding PCT application No. PCT/EP2022/072041 dated Nov. 10, 2022.

*Primary Examiner* — Imani N Hayman
(74) *Attorney, Agent, or Firm* — McDonnell Boehnen Hulbert & Berghoff LLP

(57) ABSTRACT

A medicament delivery device (1) comprising: a tubular housing (3) extending along an axis (L), wherein the housing (3) has a proximal end (3*a*) provided with a proximal opening, and a distal end (3*b*), a delivery member cover (5) configured to be axially movable along the axis (L) relative to the housing (3) from an extend position, towards which the delivery member cover (5) is biased and in which the delivery member cover (5) protrudes from the proximal opening, to a retracted position, and a drive assembly arranged in the housing (3) and configured to be activated to initiate medicament delivery by movement of the delivery member cover (5) from the extended position towards the retracted position, wherein the housing (3) has an outer surface provided with a plurality of ribs (7) extending from the proximal end (3*a*) in a direction towards the distal end (3*b*).

14 Claims, 3 Drawing Sheets

(56) References Cited

U.S. PATENT DOCUMENTS

| | | | |
|---|---|---|---|
| 10,398,854 | B2 | 9/2019 | Fenster |
| 10,709,849 | B2 | 7/2020 | Bitar |
| 2003/0229308 | A1 | 12/2003 | Tsals |
| 2005/0101919 | A1 | 5/2005 | Brunnberg |
| 2005/0261634 | A1 | 11/2005 | Karlsson |
| 2011/0202011 | A1 | 8/2011 | Wozencroft |
| 2014/0114247 | A1 | 4/2014 | Karlsson |
| 2014/0135706 | A1 | 5/2014 | Rubinstein |
| 2016/0129198 | A1 | 5/2016 | Bitar |
| 2019/0022334 | A1 | 1/2019 | Roberts |
| 2020/0289753 | A1 | 9/2020 | Andre |

FOREIGN PATENT DOCUMENTS

| | | | |
|---|---|---|---|
| EP | 2326368 | B1 | 3/2018 |
| EP | 3320932 | A1 | 5/2018 |
| JP | H3216566 | A | 9/1991 |
| JP | H3223479 | A | 10/1991 |
| JP | H3230183 | A | 10/1991 |
| WO | 2013152323 | A1 | 10/2013 |
| WO | 2014198793 | A1 | 12/2014 |
| WO | 2014198794 | A1 | 12/2014 |
| WO | 2017037470 | A1 | 3/2017 |
| WO | 2017207224 | A1 | 12/2017 |
| WO | 2017223354 | A1 | 12/2017 |
| WO | 2020173997 | A1 | 9/2020 |
| WO | 2020219672 | A1 | 10/2020 |

MEDICAMENT DELIVERY DEVICE

CROSS-REFERENCE TO RELATED APPLICATIONS

The present application is a U.S. National Phase Application pursuant to 35 U.S.C. § 371 of International Application No. PCT/EP2022/072041 filed Aug. 4, 2022 which claims priority to (i) U.S. Provisional Application Ser. No. 63/232,750 filed Aug. 13, 2021, and (ii) European Patent Application No. 21194047.3 filed Aug. 31, 2021. The entire disclosure contents of these applications are herewith in or by reference into the present application.

TECHNICAL FIELD

The present disclosure generally relates to a medicament delivery device.

BACKGROUND

Medicament delivery devices, such as autoinjectors and manual injectors, often have a needle shield that extends in the forward direction from the housing. The needle shield protects the needle from exposure before medicament delivery. The needle shield may be arranged to move along the longitudinal axis of the housing further into the housing when the medicament delivery device is pushed towards the injection site. The needle is thus exposed so that it can penetrate the patient's skin. For autoinjectors, this movement of the needle shield may cause the medicament delivery device to become activated to discharge medicament via the needle.

Medicament delivery devices of the types mentioned above on the market today do generally not take obese patient skin conditions into account in their designs. During medicament delivery, the interaction between the medicament delivery device with the folding skin in obese patients creates friction which results in that a higher activation force is required. In other words, a larger force is required to push the needle shield into the housing. Some patients with obesity may suffer from impaired dexterity and/or reduced strength, making it challenging to administer medication.

SUMMARY

An object of the present disclosure is to provide a medicament delivery device which solves, or at least mitigates, problems of the prior art.

There is hence according to a first aspect provided a medicament delivery device comprising: a tubular housing extending along an axis, wherein the housing has a proximal end provided with a proximal opening, and a distal end, a delivery member cover configured to be axially movable along the axis relative to the housing from an extend position, towards which the delivery member cover is biased and in which the delivery member cover protrudes from the proximal opening, to a retracted position, and a drive assembly arranged in the housing and configured to be activated to initiate medicament delivery by movement of the delivery member cover from the extended position towards the retracted position, wherein the housing has an outer surface provided with a plurality of ribs extending from the proximal end in a direction towards the distal end.

Since less surface of the housing will be in contact with an obese patient's folded skin when the medicament delivery device is pushed towards the site of injection, the friction will be lower. The amount of force required to activate the medicament delivery device by pushing the delivery member cover into the housing is therefore reduced. In particular, the recesses formed between the ribs help reduce the friction on the outer surface when the housing is moving toward the skin during a medicament delivery operation, as it is expected that fat tissue will not move in between the ribs.

In the present disclosure, when the term "distal direction" is used, this refers to the direction pointing away from the dose delivery site during use of the medicament delivery device. When the term "distal part/end" is used, this refers to the part/end of the delivery device, or the parts/ends of the members thereof, which under use of the medicament delivery device is/are located furthest away from the dose delivery site. Correspondingly, when the term "proximal direction" is used, this refers to the direction pointing towards the dose delivery site during use of the medicament delivery device.

When the term "proximal part/end" is used, this refers to the part/end of the delivery device, or the parts/ends of the members thereof, which under use of the medicament delivery device is/are located closest to the dose delivery site.

Further, the term "longitudinal", "longitudinally", "axially" or "axial" refer to a direction extending from the proximal end to the distal end, typically along the device or components thereof in the direction of the longest extension of the device and/or component.

Similarly, the terms "transverse", "transversal" and "transversally" refer to a direction generally perpendicular to the longitudinal direction.

Further, the terms "circumference", "circumferential", or "circumferentially" refer to a circumference or a circumferential direction relative to an axis, typically a central axis extending in the direction of the longest extension of the device and/or component. Similarly, "radial" or "radially" refer to a direction extending radially relative to the axis, and "rotation", "rotational" and "rotationally" refer to rotation relative to the axis.

According to one embodiment the ribs extend axially or helically towards the distal end.

According to one embodiment the ribs are formed between pairs of recesses in the outer surface of the housing. Each rib may thus be formed by a wall separating adjacent recesses.

According to one embodiment the ribs have the same radial thickness as the housing has outside the recesses.

The diameter of the housing may have the same size at the distal end as in a region of the housing which is not provided with any ribs.

According to one embodiment the ribs extend radially from the outer surface of the housing, wherein the ribs have a greater radial thickness than the housing.

According to one embodiment the ribs are distributed around the circumference of the housing.

According to one embodiment the ribs are distributed evenly around the circumference of the housing.

According to one embodiment the ribs are provided only along a minority of the length between the proximal end and the distal end of the housing.

The ribs may for example extend from the proximal end to not more than ⅓, such as not more than ¼, such as not more than ⅕, such as not more than ⅙ of the distance measured from the first end to the second end of the housing.

According to one embodiment the delivery member cover has a proximal end that is in level with the proximal end of the housing when the delivery member cover is in the retracted position. The delivery member cover may thus be fully received by the housing when the delivery member cover is in the retracted position.

According to one embodiment the ribs are made of a plastic material or a metal material.

The ribs may be made of a material which has lower friction than the material of the rest of the housing.

The recesses between the ribs may according to one variation be made of the same material as the ribs. This material may have a lower friction than the material of the rest of the housing.

The ribs may be made of a different material than the rest of the housing.

According to one embodiment the ribs are wedge shaped with an increasing thickness towards the distal end. A proximal end portion of the housing provided with the ribs may thus be chamfered. The proximal end portion may taper in a direction towards the proximal end.

According to one embodiment the medicament delivery device is an autoinjector or a manual injector.

According to one embodiment the drive assembly comprises: a plunger rod biased towards the proximal end of the housing, and configured to be moved linearly inside the housing from an initial position to a final position, and an actuation mechanism configured to hold the plunger rod in the initial position, wherein the actuation mechanism is configured to interact with the delivery member cover when the delivery member cover is moved from the extended position towards the retracted position, causing the actuation mechanism to disengage from the plunger rod and the plunger rod to move towards the final position.

There is according to a second aspect of the present disclosure provided a tubular housing for a medicament delivery device, the tubular housing extending along an axis wherein the housing has a proximal end provided with a proximal opening, and a distal end, wherein the housing has an outer surface provided with a plurality of ribs extending from the proximal end in a direction towards the distal end.

According to one embodiment ribs extend axially or helically towards the distal end.

According to one embodiment the ribs are formed between pairs of recesses in the outer surface of the housing.

According to one embodiment the ribs have the same radial thickness as the housing has outside the recesses.

According to one embodiment the ribs extend radially from the outer surface of the housing, wherein the ribs have a greater radial thickness than the housing.

According to one embodiment the ribs are distributed around the circumference of the housing.

According to one embodiment the ribs are distributed evenly around the circumference of the housing.

According to one embodiment the ribs are provided only along a minority of the length between the proximal end and the distal end of the housing.

According to one embodiment the ribs are made of a plastic material or a metal material.

According to one embodiment the ribs are wedge shaped with an increasing thickness towards the distal end.

Generally, all terms used in the claims are to be interpreted according to their ordinary meaning in the technical field, unless explicitly defined otherwise herein. All references to "a/an/the member, apparatus, component, means, etc." are to be interpreted openly as referring to at least one instance of the member, apparatus, component, means, etc., unless explicitly stated otherwise.

BRIEF DESCRIPTION OF THE DRAWINGS

The specific embodiments of the inventive concept will now be described, by way of example, with reference to the accompanying drawings, in which.

DETAILED DESCRIPTION

The inventive concept will now be described more fully hereinafter with reference to the accompanying drawings, in which exemplifying embodiments are shown. The inventive concept may, however, be embodied in many different forms and should not be construed as limited to the embodiments set forth herein; rather, these embodiments are provided by way of example so that this disclosure will be thorough and complete, and will fully convey the scope of the inventive concept to those skilled in the art. Like numbers refer to like members throughout the description.

Figure 1:
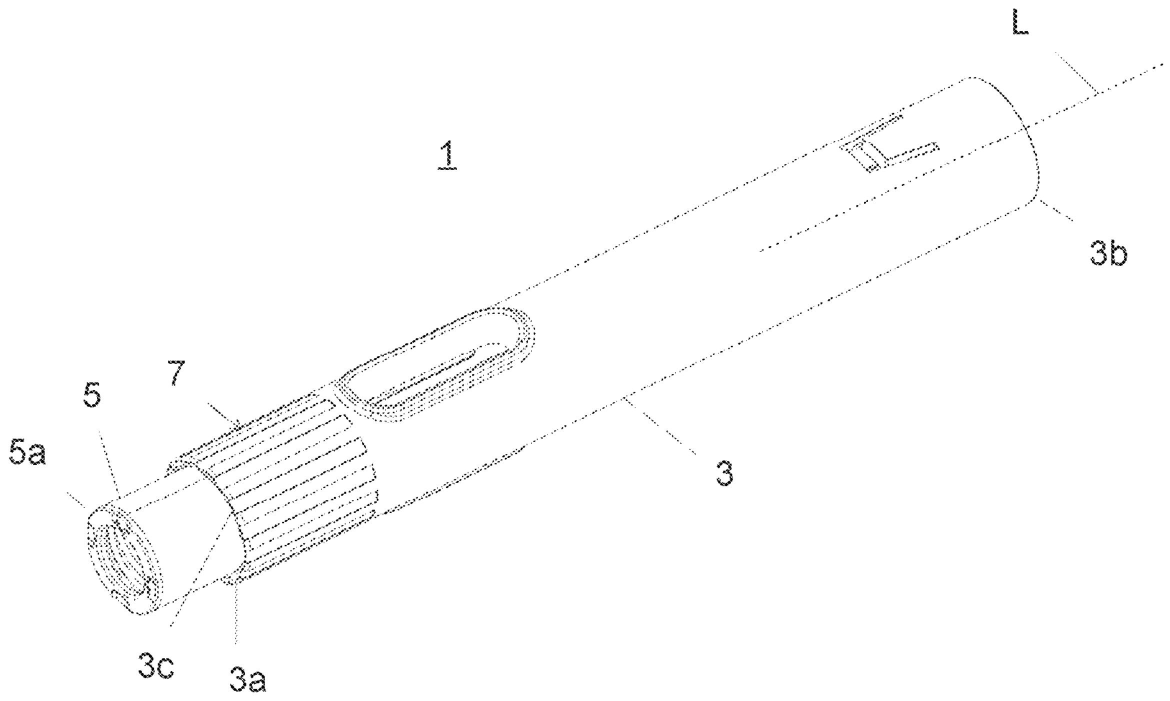
FIG. 1 is a perspective view of a schematic example of a medicament delivery device with its delivery member cover in an extended position.

FIG. 1 shows an example of a medicament delivery device 1. The medicament delivery device 1 may be an autoinjector or a manual injector.

The medicament delivery device 1 comprises a housing 3. The housing 3 is tubular. The housing 3 extends along an axis L, which is the longitudinal axis of the tubular shaped housing 3.

The housing 3 has a proximal end 3*a* and a distal end 3*b*. The housing 3 has a body which extends between the proximal end 3*a* and the distal end 3*b*. The proximal end 3*a* has a proximal surface or edge 3*c* that extends radially from the outer surface of the housing 3 to the inner surface of the housing 3.

The medicament delivery device 1 comprises a delivery member cover 5. The delivery member cover 5 may be generally tubular or tubular. The delivery member cover 5 is arranged in the housing 3 and extends proximally from a proximal opening 3*d* (shown in FIG. 3) of the housing 3.

The delivery member cover 5 is configured to be moved linearly relative to the housing 3 along the axis L. The delivery member cover 5 is configured to be moved linearly from an extended position shown in FIG. 1 to a retracted position relative to the housing 3 shown in FIG. 2. In the retracted position the delivery member cover 5 is received further by the housing 3.

The delivery member cover 5 is biased towards the extended position.

The delivery member cover 5 has a proximal end 5*a* which when the delivery member cover 5 is in the retracted position may be in level with the proximal end 3*a* of the housing 3.

The housing 3 comprises a plurality of ribs 7 extending from the proximal end 3*a* of the housing 3 towards the distal end 3*b*. The ribs 7 are provided on the outer surface of the housing 3.

The medicament delivery device 1 comprises a drive assembly (not shown) arranged in the housing 3. The drive assembly may be any drive assembly used in an autoinjector or a manual injector which activates or triggers medicament delivery by movement of the delivery member cover 5 from the extended position towards the retracted position. Examples of suitable drive assemblies are for example disclosed in WO02047746, WO2011123024 WO2019011688, WO2019011689, WO2019011690, and WO2019063267 incorporated herein by reference.

For completeness, one example of a drive assembly will be briefly described in the following.

The drive assembly may comprise a plunger rod (not shown) biased towards the proximal end 3*a* of the housing 3. The plunger rod is configured to be moved linearly inside the housing 3 from an initial position in which the plunger rod is arranged prior to medicament delivery, to a final position, which the plunger rod attains when medicament delivery has been completed.

The drive assembly may comprise an actuation mechanism configured to hold the plunger rod in the initial position when the delivery member cover 5 is in the extended position. The actuation mechanism is configured to interact with the delivery member cover 5 when the delivery member cover 5 is moved from the extended position towards the retracted position, causing the actuation mechanism to disengage from the plunger rod and the plunger rod to move towards the final position.

The actuation mechanism may for example comprise a rear end cap having a body extending towards the proximal end 3*a* of the housing 3. The rear end cap may comprise radially flexible arms configured to engage with the plunger rod when the plunger rod is in the initial position to thereby prevent the plunger rod from moving towards the final position.

The actuation mechanism may comprise a rotator provided around the body of the rear end cap, configured to prevent the arms to flex radially outwards when the delivery member cover 5 is in the extended position. The rotator is configured to be rotated by the delivery member cover 5, which may be rotationally locked relative to the housing 3, when the delivery member cover 5 is moved linearly from the extended position to the retracted position. The rotator may have windows or recesses on its inner surface that align with a respective arm of the rear end cap when the rotator is rotated by the delivery member cover 5, enabling the arms to flex out radially thus disengaging from the plunger rod which is released and moved towards the final position.

Figure 3:
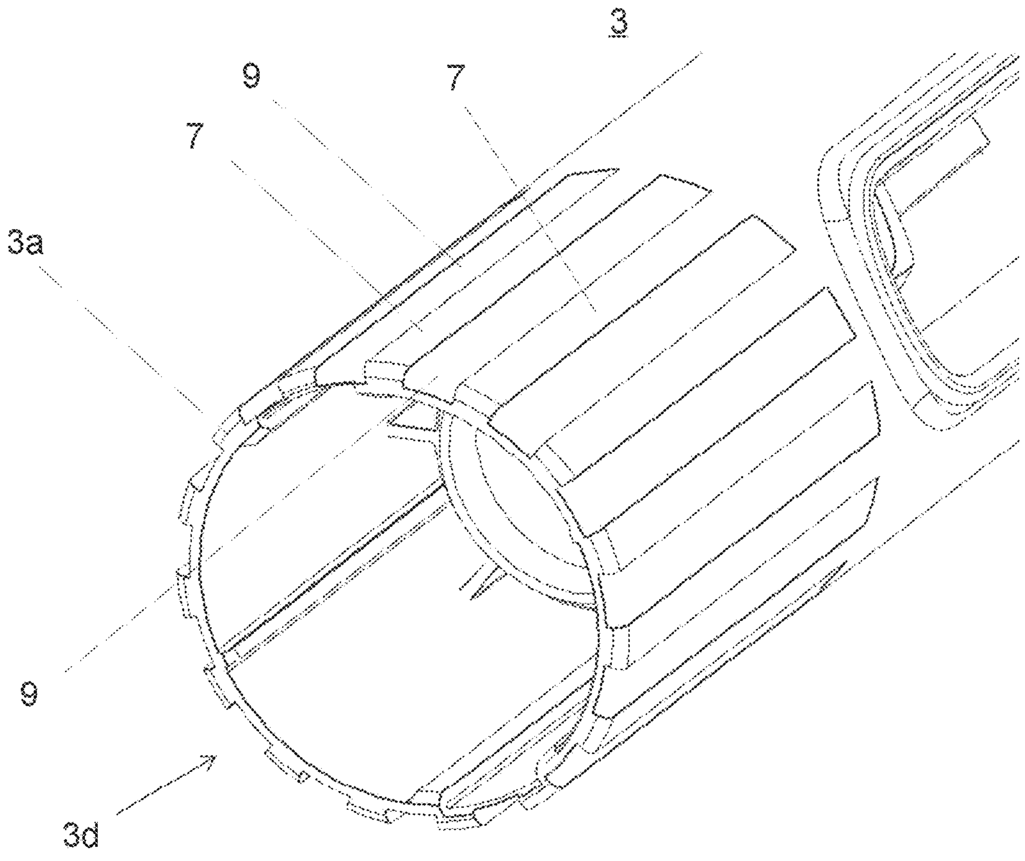
FIG. 3 is a close-up view of a proximal end of the medicament delivery device in FIG. 1.

FIG. 3 shows a close-up view of a proximal portion of the housing 3 comprising the ribs 7 and a plurality of recesses 9 separating the ribs 7. There is a recess 9 between each adjacent pair of ribs 7.

The ribs 7 are distributed around the circumference of the housing 3. The ribs 7 may be evenly distributed around the circumference of the housing 3 as in the example shown in FIG. 3, or they may be distributed in an uneven manner.

All the ribs 7 may have the same width, the width being the dimension of a rib 7 in the circumferential direction of the housing 3. Alternatively, one or more of the ribs 7 may have a width that differs from the width of one or more of the other ribs 7.

According to one example, the width of at least one, for example all, of the ribs 7 may be constant in the axial direction.

According to one example, the width of at least one, for example all, of the ribs 7 may vary in the axial direction. The width of the recesses 9 may thus also vary in this case. The recesses 9 may for example be wider closer to the proximal end 3*a*, and they may narrow down as the recesses 9 extend towards the distal end 3*b*. Alternatively, the widths of the recesses 9 may be narrower closer to the proximal end 3*a* and increase as the recesses 9 extend towards the distal end 3*b*.

The ribs 7 extend all the way to the proximal end 3*a* of the housing 3. The ribs 7 extend in the axial direction for a minority, that is less than 50%, of the length/distance between the proximal end 3*a* and the distal end 3*b*.

In the example shown in FIG. 3, the ribs 7 extend axially and are parallel with the axis L along their entire extension. The ribs 7 could alternatively be arranged helically or in a waveshape/undulating as they extend from the proximal end 3*a* towards the distal end 3*b*.

According to the example in FIG. 3, the ribs 7 extend radially only up to a level where they are flush with the outer surface of the housing 3. The ribs 7 do hence not increase the diameter of the housing 3. The ribs 7 may have the same radial thickness as the rest of the housing 3 outside of the recesses 9. In the recesses 9, the housing 3 has a radial thickness which is thinner than that of the housing 3 in a region without ribs 7.

The ribs 7 may for example be made of a plastic material or metal. The ribs 7 may be made of the same material as the rest of the housing 3, or they may be made of a material which differs from the material of the rest of the housing 3. The ribs 7 may for example be made of a material, or provided with a coating, that has lower friction than the outer surface of the housing 3.

Figure 2:
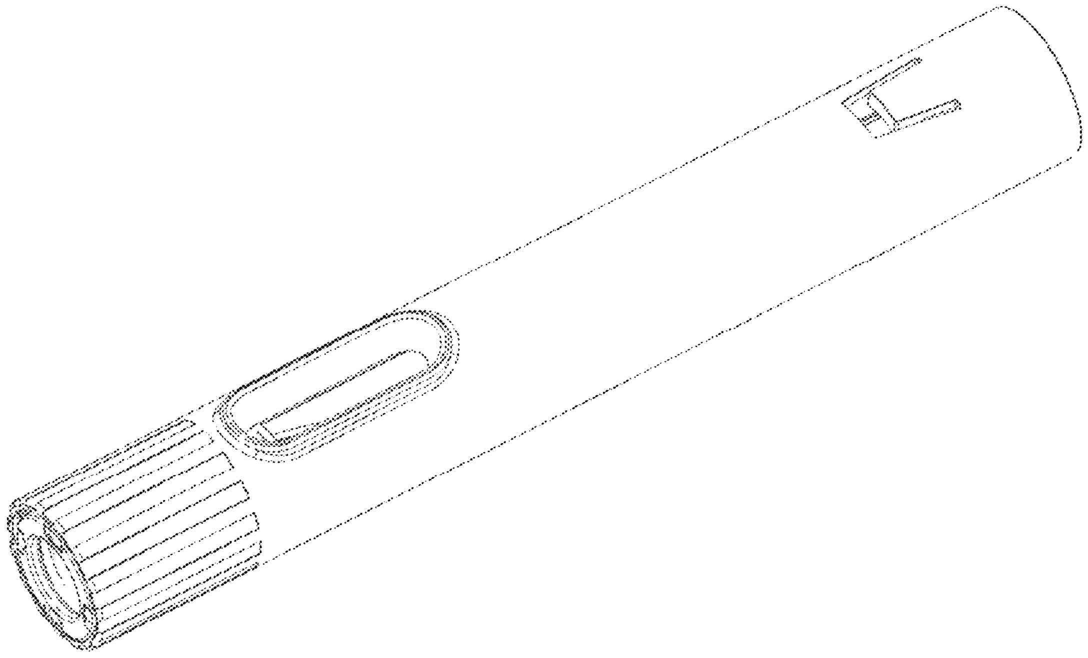
FIG. 2 is a perspective view of the medicament delivery device in FIG. 1 with the delivery member cover in the retracted position.
Figure 4:
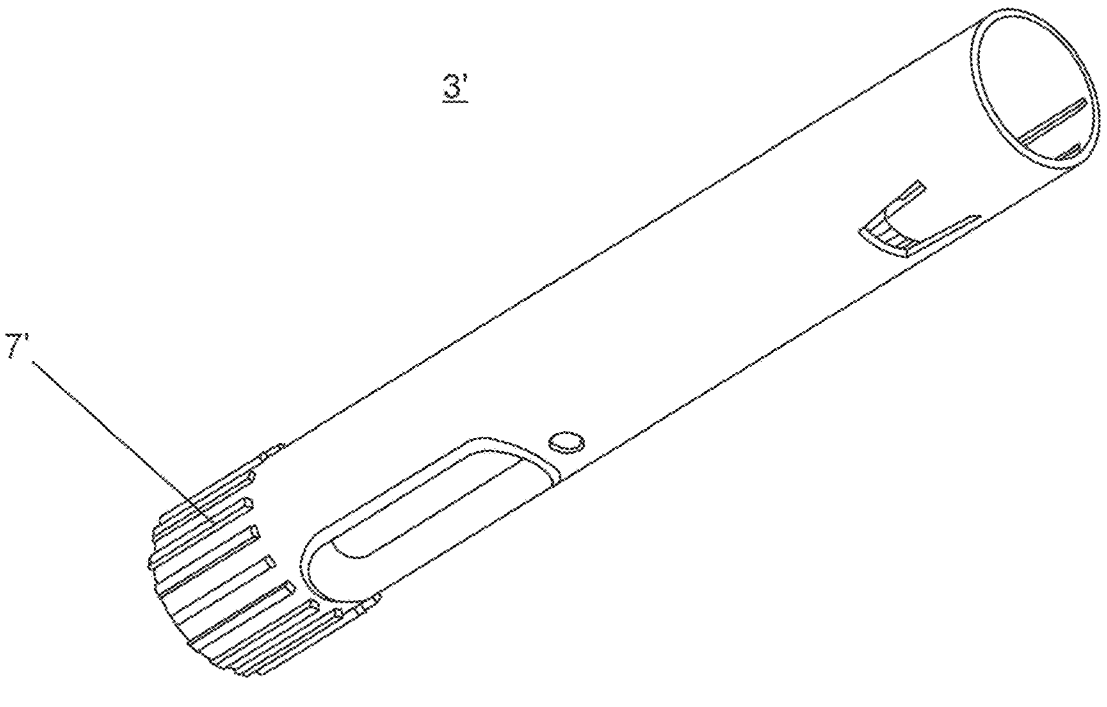
FIG. 4 shows another example of a housing for a medicament delivery device.

FIG. 4 shows an alternative example of the housing 3. The housing 3' shown in FIGS. 1-3 is similar to the housing 3. The ribs 7' however protrude relative to the outer surface of the housing 3'. The ribs 7' thus extend radially from the outer surface of the housing 3'. The ribs therefore have a greater radial thickness or dimension than the housing 3'. Variations of the types described above with regards to the housing 3 are also envisaged for the housing 3'. Thus, the ribs 7' may instead of extending axially extend helically or in an undulating fashion, their widths may vary or be constant, etc.

Figure 5A:
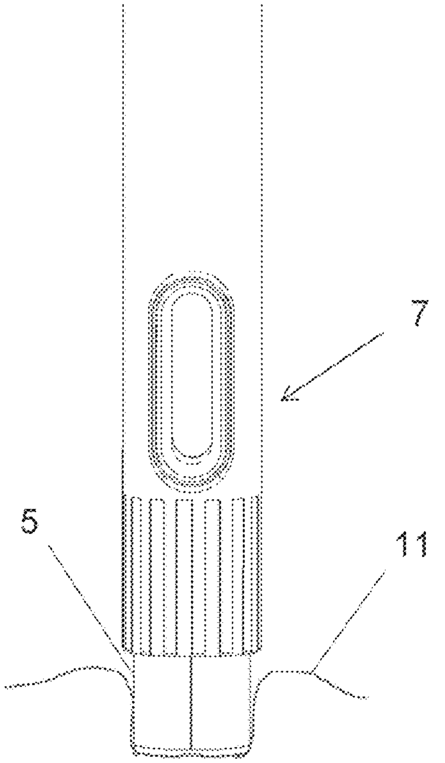
FIGS. 5A-5C show side views of the medicament delivery device in FIG. 1 at different stages of medicament delivery.
Figure 5B:
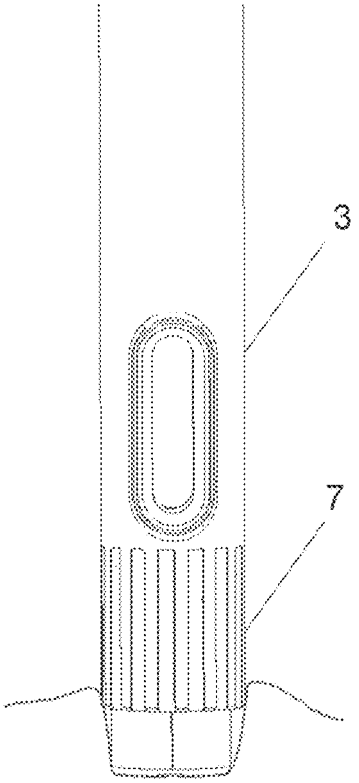
Figure 5C:
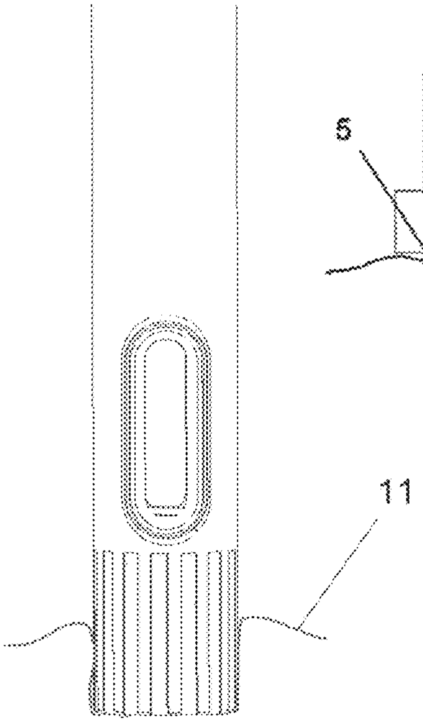

FIGS. 5A-5C show the medicament delivery device 1 in various stages in use.

In FIG. 5A, the medicament delivery device 1 has been placed against a site of injection, which in this case is the skin of a patient with obesity. The delivery member cover 5 has sunk into the skin and fat tissue 11 of the patient.

In FIG. 5B, the medicament delivery device 1 has been further pushed against the skin and fat tissue 11, causing it to envelope the delivery member cover 5 which has now been partially moved from the extended position towards the retracted position. In the example, the skin and fat tissue 11 now also bears against the outer surface of the housing 3. Due to the ribs 7, the contact between the housing 3 and the skin is reduced, resulting in less friction and thus less force required to push the delivery member cover 5 further into the housing 3 towards the retracted position.

In FIG. 5B, the delivery member cover 5 has been fully moved into the housing 3 as it has attained its retracted position. Here, the housing 3 with the ribs 7 at its proximal end portion has sunk further into the skin and fat tissue 11.

Optionally, the distance which the delivery member cover protrudes from the housing can be increased compared to that shown in the figures, for example by shortening the length of the housing whilst keeping the rest of the device unchanged. This can reduce the activation force.

Figure 6:
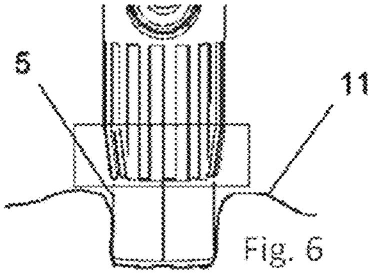
FIG. 6 shows an example with a tapered proximal end of the housing.

Optionally, the proximal end of the housing is tapered. This can reduce the diameter difference between the housing and the delivery member cover. This can reduce the activation force. An example of a tapered proximal end of the housing is shown in FIG. 6, with the tapered proximal end highlighted in a rectangular box in FIG. 6.

The inventive concept has mainly been described above with reference to a few examples. However, as is readily appreciated by a person skilled in the art, other embodiments than the ones disclosed above are equally possible within the scope of the inventive concept, as defined by the appended claims.

The invention claimed is:

1. A medicament delivery device, comprising:

a tubular housing extending along an axis, wherein the housing has a proximal end provided with a proximal opening, and a distal end;

a delivery member cover configured to be axially movable along the axis relative to the housing from an extended position, towards which the delivery member cover is biased and in which the delivery member cover protrudes from the proximal opening, to a retracted position; and a drive assembly arranged in the housing and configured to be activated to initiate medicament delivery by movement of the delivery member cover from the extended position towards the retracted position, wherein the housing has an outer surface provided with a plurality of ribs extending from the proximal end in a direction towards the distal end, wherein the ribs are formed between pairs of recesses in the outer surface of the housing.

2. The medicament delivery device of claim 1, wherein the ribs extend axially or helically towards the distal end.

3. The medicament delivery device of claim 1, wherein the ribs have the same radial thickness as the housing has outside the recesses.

4. The medicament delivery device of claim 1, wherein the ribs extend radially from the outer surface of the housing, wherein the ribs have a greater radial thickness than the housing.

5. The medicament delivery device of claim 1, wherein the ribs are distributed around the circumference of the housing.

6. The medicament delivery device of claim 1, wherein the ribs are distributed evenly around the circumference of the housing.

7. The medicament delivery device of claim 1, wherein the ribs are provided only along a minority of the length between the proximal end and the distal end of the housing.

8. The medicament delivery device of claim 1, wherein the delivery member cover has a proximal end that is in level with the proximal end of the housing when the delivery member cover is in the retracted position.

9. The medicament delivery device of claim 1, wherein the ribs are made of a plastic material or a metal material.

10. The medicament delivery device of claim 1, wherein the ribs are wedge shaped with an increasing thickness towards the distal end.

11. The medicament delivery device of claim 1, wherein the medicament delivery device is an autoinjector or a manual injector.

12. The medicament delivery device of claim 1, wherein the drive assembly comprises:

a plunger rod biased towards the proximal end of the housing, and configured to be moved linearly inside the housing from an initial position to a final position, and an actuation mechanism configured to hold the plunger rod in the initial position, wherein the actuation mechanism is configured to interact with the delivery member cover when the delivery member cover is moved from the extended position towards the retracted position, causing the actuation mechanism to disengage from the plunger rod and the plunger rod to move towards the final position.

13. The medicament delivery device of claim 1, wherein the ribs are made of a material with a lower friction than a material of the tubular housing.

14. A medicament delivery device, comprising:

a tubular housing extending along an axis, wherein the housing has a proximal end provided with a proximal opening, and a distal end;

a delivery member cover configured to be axially movable along the axis relative to the housing from an extended position, towards which the delivery member cover is biased and in which the delivery member cover protrudes from the proximal opening, to a retracted position; and a drive assembly arranged in the housing and configured to be activated to initiate medicament delivery by movement of the delivery member cover from the extended position towards the retracted position, wherein the housing has an outer surface provided with a plurality of ribs extending from the proximal end in a direction towards the distal end, wherein the ribs are wedge shaped with an increasing thickness towards the distal end.

* * * * *